US00PP16277P2

(12) United States Plant Patent
Verhoef

(10) Patent No.: US PP16,277 P2
(45) Date of Patent: Feb. 21, 2006

(54) ***CORTADERIA* PLANT NAMED 'SPLENDID STAR'**

(50) Latin Name: *Cortaderia selloana*
Varietal Denomination: Splendid Star

(76) Inventor: Gijsbertus Verhoef, Burg. Smitweg 37, Hazerswoude (NL), 23G1 NE ( * ) Notice: Subject to any disclaimer, the term of this patent is extended or adjusted under 35 U.S.C. 154(b) by 178 days.

(21) Appl. No.: 10/848,319

(22) Filed: May 18, 2004

(51) Int. Cl.
*A01H 5/00* (2006.01)

(52) U.S. Cl. ..... Plt./292

(58) Field of Classification Search ..... Plt./292, Plt./384

See application file for complete search history.

*Primary Examiner*—Anne Marie Grunberg
*Assistant Examiner*—Annette H Para

(57) ABSTRACT

A new cultivar of *Cortaderia* plant named 'SPLENDID STAR' that is characterized by dwarf, spreading habit, variegated golden foliage, and silver-white plumes in fall. In combination these traits set 'SPLENDID STAR' apart from all other existing varieties of *Cortaderia* known to the inventor.

2 Drawing Sheets

Genus: *Cortaderia*. Species: *selloana*.
Denomination: SPLENDID STAR.

BACKGROUND OF THE INVENTION

The present invention relates to a new and distinct cultivar of pampas grass, a perennial grass grown for use as an ornamental in the landscape. The new cultivar is known botanically as *Cortaderia selloana* and will be referred to hereinafter by the cultivar name 'SPLENDID STAR'.

'SPLENDID STAR' was discovered by the inventor, as a chance sport in 1997 in a cultivated area of Hazerswoude, The Netherlands. The parent plant is *Cortaderia selloana* 'Pumila' (unpatented). 'SPLENDID STAR' was selected by the inventor as an individual variegated branch sport found growing on a single plant of *Cortaderia selloana* 'Pumila'. Selection was based on the unique golden variegated foliage. 'SPLENDID STAR' is distinguishable from the parent plant by golden variegated foliage.

'SPLENDID STAR' is an ornamental grass that performs best in well-drained soil, full sun or partial shade, and minimal to moderate water. The closest comparison plants are *Cortaderia selloana* 'Gold Band' (unpatented) and the parent plant *Cortaderia selloana* 'Pumila'. 'SPLENDID STAR' is distinguishable from 'Gold Band' by dwarf size, and is distinguishable from 'Pumila' by golden variegation. The foliage of 'Pumila' is green. No other existing dwarf, variegated *Cortaderia selloana* is known to the inventor.

Asexual reproduction of the new cultivar 'SPLENDID STAR' was first accomplished by the inventor in a cultivated area of Hazerswoude, The Netherlands in 1997. The method of propagation used was division. Since that time the unique characteristics of the new cultivar have been determined stable and are reproduced true to type in successive generations.

An application for a grant of European Community Plant Variety Rights for 'SPLENDID STAR' was filed on Sep. 17, 2001, Ser. No. 2001/1485.

Plants of 'SPLENDID STAR' were first made available to the public, in Europe, on Jun. 9, 2003.

SUMMARY OF THE INVENTION

The following traits have been repeatedly observed and represent the distinguishing traits of 'SPLENDID STAR'. These traits in combination distinguish the new cultivar from all other existing varieties of *Cortaderia* known to the inventor. 'SPLENDID STAR' has not been tested under all possible conditions and phenotypic differences may be observed with variations in environmental, climatic and cultural conditions.

1. *Cortaderia* 'SPLENDID STAR' is a perennial.
2. *Cortaderia* 'SPLENDID STAR' is an ornamental grass for use in containers, patios, rock gardens and the landscape.
3. *Cortaderia* 'SPLENDID STAR' exhibits a dwarf, spreading habit.
4. *Cortaderia* 'SPLENDID STAR' exhibits an elegant pendulous form.
5. *Cortaderia* 'SPLENDID STAR' is propagated by the method of division.
6. *Cortaderia* 'SPLENDID STAR' reaches 80–100 cm. in height and 80–100 cm. in width at maturity.
7. *Cortaderia* 'SPLENDID STAR' exhibits a profusion of silver-white flower plumes in fall.
8. *Cortaderia* 'SPLENDID STAR' is hardy to USDA Zone 7.

BRIEF DESCRIPTION OF THE DRAWINGS

The accompanying color drawings, labeled as FIG. 1 and FIG. 2, illustrate the overall appearance of the new *Cortaderia* cultivar 'SPLENDID STAR' showing the colors as true as it is reasonably possible to obtain in colored reproductions of this type. Colors in the drawings may differ from the color values cited in the detailed botanical description, which accurately describe the actual colors of the new variety 'SPLENDID STAR'. The drawings were made using conventional techniques and although colors may appear different from actual colors due to light reflectance they are as accurate as possible by conventional photography.

The drawing labeled as FIG. 1 illustrates a three year old entire plant, in flower, from a side perspective.

Figure 1:
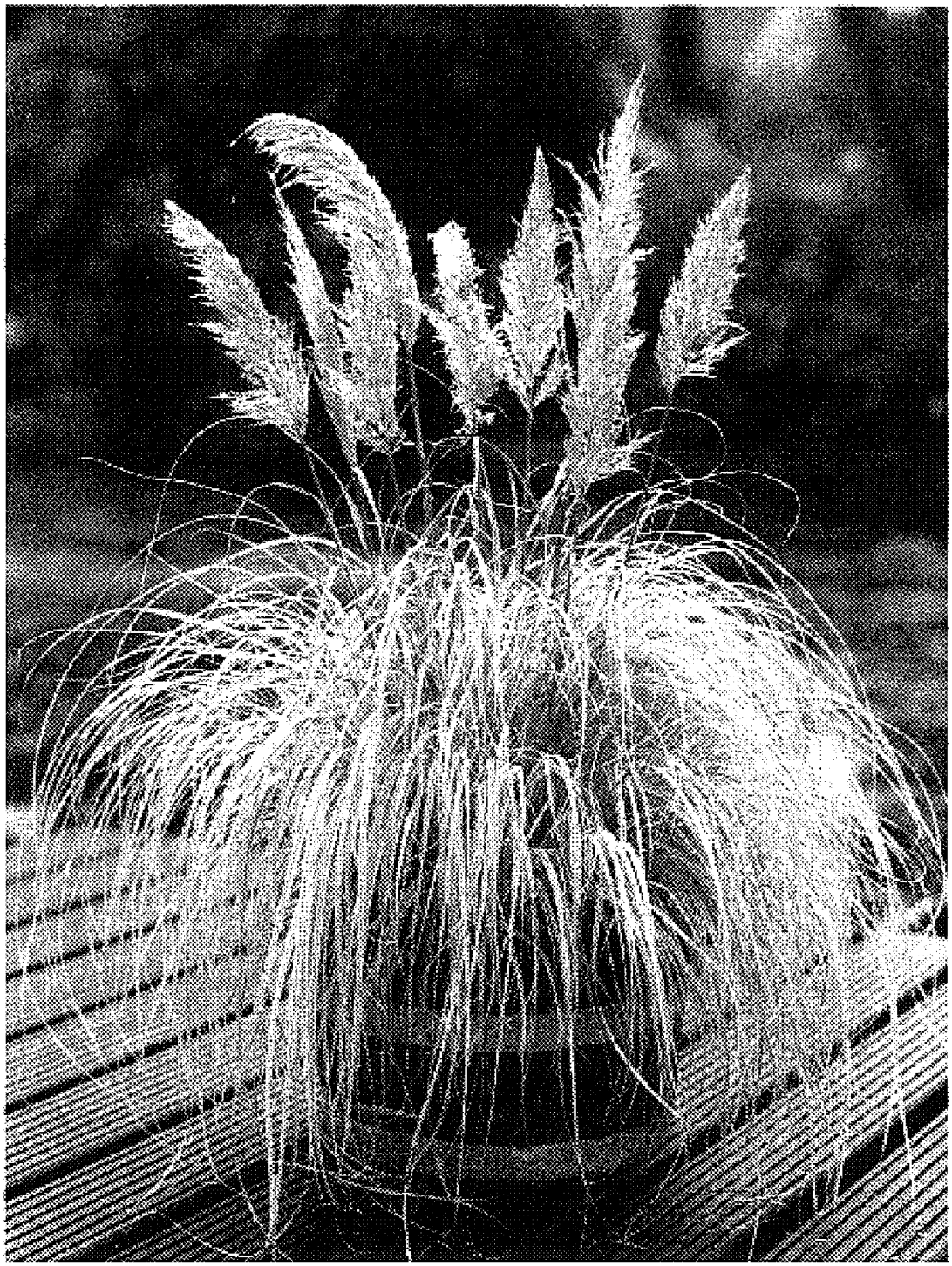
Figure 2:
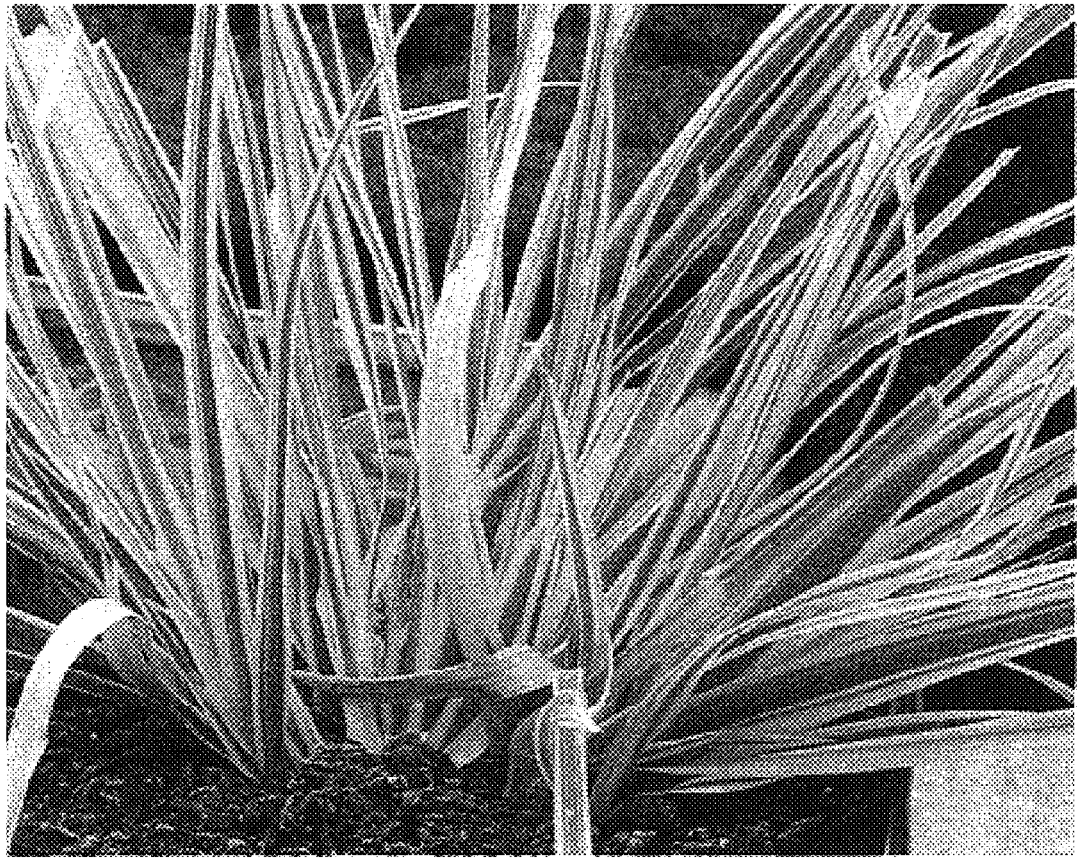

The drawing labeled as FIG. 2 is a close-up view of the foliage, showing the basal stem arrangement and the variegated coloration of the leaf blades.

BOTANICAL DESCRIPTION OF THE PLANT

The following is a detailed description of the new *Cortaderia* cultivar 'SPLENDID STAR'. Data was collected by the inventor in Hazerswoude, The Netherlands and collected from 24-month-old 5-liter container plants grown out-of-doors. Data was collected in the month of September. The average daytime temperatures ranged from 13–25° Centigrade and the average nighttime temperatures ranged from 5–14° Centigrade. The light level was normal outdoor light and there were no growth retardants or photoperiodic treatments applied. The color determinations are in accordance with the 2001 Royal Horticultural Society Colour Chart of London, England, except where general color terms of ordinary dictionary significance are used. Growing conditions are similar to other *Cortaderia* varieties.

Botanical classification: *Cortaderia selloana* 'SPLENDID STAR'.
Species: *selloana*.
Type: Perennial.
Plant shape: Flattened globular with pendulous leaves.
Commercial classification: Grass.
Common name: Pampas grass.
Rooting habit: Fleshy and thick.
Propagation: Propagated by division.
Use: Ornamental grass for use in containers, patios, rock gardens and the landscape.
Cultural requirements: Provide minimal to moderate water, well-drained loam soil and full sun to partial shade.
Parentage: *Cortaderia selloana* 'SPLENDID STAR' is a chance sport discovered as a variegated branch off an individual plant in a crop of *Cortaderia selloana* 'Pumila'.
*Parent plant.*—*Cortaderia selloana* 'Pumila'.
Flowering season: Fall.
Plant habit: Dwarf and spreading.
Form: Pendulous.
Vigor: Moderate.
Growth rate: Approximately 20 cm. per month in spring.
Height: 45 cm. in a 5-liter container and 80–100 cm. in height at maturity.
Width: 65–70 cm. in a 5-liter container and 80–100 cm. in width at maturity.
Roots: Thick and fleshy.
High temperature tolerance: Up to 35° Centigrade.
Hardiness: Hardy to USDA Zone 7.
Crop time: Approximately 9–12 months are required from the time of division to reach a commercial 5-liter size container.
Disease and pest resistance and susceptibility: Susceptibility and resistance is typical to other *Cortaderia* varieties.
Stem:
*Branching habit.*—Basal branching with no lateral stems.
*Number of basal stems.*—Average number of stems is 18.
*Basal stem length.*—12 cm. in length.
*Basal stem width.*—6 mm. in width.
*Basal stem surface.*—Glabrous with dull matte appearance.
*Shape of basal stem.*—Cylindrical.
*Stem strength.*—Strong and durable.
*Stem color.*—Colors 145C, 186A and 186B are all individually present on an individual stem.
*Pubescence: Absent.*
Foliage:
*Type.*—Evergreen.
*Shape.*—Linear.
*Division.*—Simple.
*Quantity of leaves.*—An average of 9 leaves per basal stem.
*Leaf apex.*—Acuminate.
*Leaf base.*—Cuneate.
*Internode length.*—2.9 cm. between nodes.
*Leaf margin.*—Denticulate.
*Leaf aspect.*—Arching.
*Arrangement.*—Alternate.
*Leaf attachment.*—Sheathing.
*Leaf length.*—Average length of leaf is 65 cm.
*Leaf width.*—Average width of leaf is 1.1 cm.
*Leaf surface* (*adaxial and abaxial surfaces*).—Mostly glabrous but minutely puberulent at margins.
*Leaf appearance* (*adaxial and abaxial surfaces*).—Slightly shiny.
*Young leaf color* (*adaxial surface*).—Individual colors 145B, 146C, and 154C are present on an individual leaf.
*Young leaf color* (*abaxial surface*).—Individual colors 145B, 10A, 154C are present on an individual leaf.
*Mature leaf color* (*adaxial surface*).—Individual colors 137B, 146A, 11A, 160B are present on an individual leaf.
*Mature leaf color* (*abaxial surface*).—Individual colors 137B, 146A, 10A, and 10B are present on an individual leaf.
*Vein pattern.*—Parallel.
*Vein color* (*adaxial and abaxial surfaces*).—146C.
*Durability of foliage to stress.*—Highly durable.
*Stipules, tendrils and thorns.*—Absent.
Flowers:
*Flower arrangement.*—Terminal panicle.
*Inflorescence type.*—Panicle.
*Flower type.*—Single flower.
*Inflorescence dimensions.*—30 cm. in height and 11 cm. in width.
*Quantity of flowers per inflorescence.*—An average of 3000 flowers per inflorescence.
*Quantity of flowers and buds per plant.*—Over 6000.
*Flowers persistent or self-cleaning.*—Persistent.
*Bloom period.*—Blooms continuously from late September into early November.
*Response time* (*time to flower*).—Approximately 10 months.
*Rate of flower opening.*—After the first flowers open, all others on the individual plant open with 2 weeks.
*Fragrance.*—Faint fragrance present.
*Bud length.*—An average of 2 mm. in length, enclosed by 1 glume and many lemma.
*Bud diameter.*—Average of 1 mm. in diameter.
*Bud shape.*—Narrow lanceolate.
*Bud color.*—Individual colors 144C, 144D, and 156C are present on an individual bud.
*Flower aspect.*—Upright to slightly outward.
*Inflorescence shape.*—Plumous.
*Flower diameter.*—1 mm. in diameter.

*Flower height.*—4 mm. in height but enclosed by 1 glume and many lemma.

*Lastingness of flower on plant.*—Approximately 10 days.

*Petal surface.*—Glume is glabrous and lemma consists of many hairs.

*Petal arrangement.*—1 glume positioned at posterior of each flower and lemma rotate.

*Petal number.*—1 glume and approximately 50 lemma per flower.

*Petals fused or unfused.*—Unfused.

*Petal shape.*—Lemma is fibril-shaped and glume is linear.

*Petal margin.*—Margins of glume and lemma are entire.

*Petal tip* (*glume*).—Narrow acute.

*Petal length* (*glume and lemma*).—An average of 1.5 cm. in length.

*Petal width* (*glume and lemma*).—1 mm. in width.

*Petal color* (*adaxial and abaxial surface when opening*).—A combination of colors 156C and 156D.

*Petal color* (*adaxial and abaxial surface when fully opened*).—A combination of colors 156A and 156B.

*Awn.*—Average length is 9 mm. Average width is 0.2 mm. Color closest to and between greyed-white 156A and 156B.

*Petaloids.*—None observed.

*Sepals.*—None observed.

*Peduncle length.*—Average length is 70 cm.

*Peduncle width.*—Average width is 9 mm.

*Angle of peduncle.*—Average angle is 0°.

*Strength of peduncle.*—Strong and durable.

*Peduncle color.*—Colors 146C, 146B, 155A, and 155B are individually present on an individual peduncle.

*Pedicels.*—Present.

*Pedicel dimensions.*—An average of 5 mm. in length and 0.25 mm. in diameter.

*Pedicel angel.*—0° to 40°.

*Pedicel strength.*—Moderate.

*Pedicel color.*—A combination of colors 144C and 144D.

Reproductive organs:

*Stamens.*—Two in number.

*Anther shape.*—Plumose and basafixed.

*Anther length.*—0.8 mm. in length.

*Anther color.*—A combination of colors 162B and 162C.

*Amount of pollen.*—Very little pollen.

*Pollen color.*—A combination of colors 160A and 160B.

*Pistil.*—None observed.

Seed production: None observed.

It is claimed:

1. A new and distinct cultivar of *Cortaderia* plant named 'SPLENDID STAR' as described and illustrated herein.

* * * * *